United States Patent [19]

Takahama et al.

[11] Patent Number: 4,839,019
[45] Date of Patent: Jun. 13, 1989

[54] OXYGEN SENSOR

[75] Inventors: Teizo Takahama; Masahiko Masuda; Keisuke Sugimoto; Yuji Sugiyama, all of Kanagawa, Japan

[73] Assignee: Fuji Electric Co., Ltd., Kanagawa, Japan

[21] Appl. No.: 121,806

[22] Filed: Nov. 17, 1987

[30] Foreign Application Priority Data

Nov. 20, 1986 [JP] Japan .................................. 61-177537
Dec. 4, 1986 [JP] Japan .................................. 61-186952

[51] Int. Cl.$^4$ .................................. G01N 27/46
[52] U.S. Cl. .................................. 204/425; 204/412; 204/426
[58] Field of Search .................. 204/15, 421–429, 204/412

[56] References Cited

U.S. PATENT DOCUMENTS

| | | | |
|---|---|---|---|
| 4,272,331 | 6/1981 | Hetrick | 204/426 |
| 4,277,323 | 7/1981 | Muller et al. | 204/426 |
| 4,400,260 | 8/1983 | Stahl et al. | 204/429 |
| 4,505,783 | 3/1985 | Mase et al. | 204/15 |
| 4,547,281 | 10/1985 | Wang et al. | 204/426 |
| 4,570,479 | 2/1986 | Sakurai et al. | 204/426 |
| 4,571,285 | 2/1986 | Nakazawa et al. | 204/425 |
| 4,629,549 | 12/1986 | Kojima et al. | 204/425 |
| 4,639,305 | 1/1987 | Shibata et al. | 204/426 |
| 4,718,999 | 1/1988 | Suzuki et al. | 204/425 |

Primary Examiner—T. Tung
Attorney, Agent, or Firm—Finnegan, Henderson, Farabow, Garrett & Dunner

[57] ABSTRACT

A limited current type oxygen sensor comprises an oxygen ion conductive solid electrolyte, a detection element including a positive electrode and a negative electrode, and a heater element including a heater. The negative electrode is installed on one of the walls constituting a space communicating with a small hole for restricting the amount of oxygen to diffuse therethrough. The porous positive electrode and the heater are embedded in the oxygen ion conductive solid electrolyte layers.

6 Claims, 3 Drawing Sheets

OXYGEN SENSOR

BACKGROUND OF THE INVENTION

The present invention relates to limited current type oxygen sensors, and, more particularly those which can be employed effectively as oxygen deficiency monitors for use in automobiles and boilers.

U.S. patent application Ser. No. 008,655, filed Jan. 30, 1987 and assigned to the common assignee, Fuji Electric Co., Ltd., which application is hereby incorporates by reference, discloses an invention made by inventors including all the applicants of the present invention: a limited current type oxygen sensor formed with an oxygen ion conductive solid electrolyte of zirconia as shown in FIGS. 5(A) and 5(B) as represented generally by the numeral 100. The shape and area of a detection element 11 in oxygen sensor 100 are made equal to or slightly smaller than the shape and area of a space 3 in order to prevent electrical interference between detection element 11, in which ionic current flows between electrodes 1, 2 embedded in a solid electrolyte, and a heater element 12 with heaters 5 embedded in a solid electrolyte. Space 3, sandwiched between detection element 11 and heater element 12, communicates with a ssmall hole or diffusion orifice 4 for permitting ambient gas to enter the space 3. Leads 6, 7 of electrodes 1, 2 are connected to terminals 10A, 10D, respectively, whereas heater 5 is connected to terminals 10B, 10C, respectively.

In this oxygen sensor 100, the heater element 12 should be heated up high enough to overcome the thermal resistance caused by the space 3 disposed between the detection element 11 and the heater element 12 for heating the detection element 11 up to a predetermined temperature of operation of the sensor 100. Accordingly, as the amount of power required to operate sensor 100 tends to increase, the heater element 12 is heated to a high temperature to the detriment of long-term stability of the heater element 12. In addition to this disadvantage, thermal stress that occurs in the oxygen sensor 100 may ultimately damage the oxygen sensor 100 itself (as the temperature difference between the vicinity of the heater element 12 and the remaining portions of sensor 100 increases).

SUMMARY OF THE INVENTION

The present invention aims at effectively solving the aforesaid disadvantages in the prior art. Therefore, an object of the invention is to provide a limited current type oxygen sensor which can operate with reduced amounts of power by lowering the thermal resistance between the heater element and the detection element. Another object of the invention is to provide an oxygen sensor that efficiently conducts heat to a detection element including a pair of electrodes for putting an oxygen ion conductive solid electrolyte into an ion conductive state.

Another object is to minimize thermal stresses inside the sensor. Another object is to provide an oxygen sensor with stable operating performance, which is at the same time reliable and easily manufactured. A further object is to provide for a porous positive electrode of a detection element and a heater of a heater element in the oxygen sensor, which is embedded in an oxygen ion conductive solid electrolyte in a configuration such that the heat generated by the heaters is directly transmitted through the oxygen conductive solid electrolyte to the detection element.

Based upon the results of their studies and a number of experiments carried out to solve the aforesaid problems the present inventors have realized that although a conventional arrangement is to make the oxygen produced by the positive electrode readily diffuse outward by providing a negative electrode of a detection element in a space and exposing the positive electrode directly to the external ambience heretofore, the provision of a positive electrode between layers of zirconia in an oxygen sensor has not been provided. On the other hand, the electrodes of the oxygen sensor should preferably be porous rather than completely dense. Accordingly, the oxygen produced by the positive electrode can readily be diffused outward if part of the positive electrode provided between the layers of zirconia is exposed to the external ambience. Further, the present inventors have proved that the electrode obtained through the process of manufacturing electrodes described in the aforesaid U.S. patent application Ser. No. 008,655 is usable as such a porous electrode.

To achieve the foregoing objects, and in accordance with the invention as embodied and broadly described herein, a limited current type oxygen sensor is provide comprising an oxygen ion conductive solid electrolyte, a detection element with a positive and a negative electrode embedded therein, a heater element with a heater embedded therein, a space internal to the sensor defined by walls one of which is provided with a diffusion orifice for restricting the amount of oxygen to be diffused and another of which is adjacent to the negative electrode. In one embodiment of the present invention, a shielding electrode is provided between the detection and heater elements. In another embodiment, the positive electrode of the detection element is also used as a heater element.

Additional objects and advantages of the invention will be set forth in the description which follows, and in part will be obvious from the description, or may be learned by practice of the invention. The objects and advantages of the invention may be realized and obtained by means of the instrumentality and combinations particularly pointed out in the appended claims.

The accompanying drawings which are incorporated in and constitute a part of the specification, illustrate preferred embodiments of the invention and, together with the summary description given above and the detailed description of the preferred embodiments including the appended claims given below, serve to explain the principles of the invention.

DETAILED DESCRIPTION OF THE INVENTION

Figure 1A:
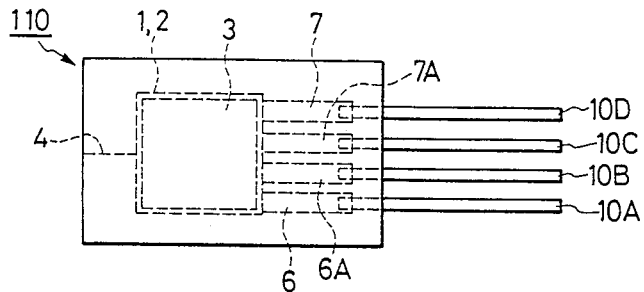
FIGS. 1(A) and 1(B) are top and sectional views, respectively, of a limited current type oxygen sensor incorporating the teachings of the present preferred embodiments of the invention.

Referring now to the accompanying drawings, embodiments of the present invention will be described. In the drawings, excepting FIG. 4, like reference numerals refer to like parts.

Figure 1B:
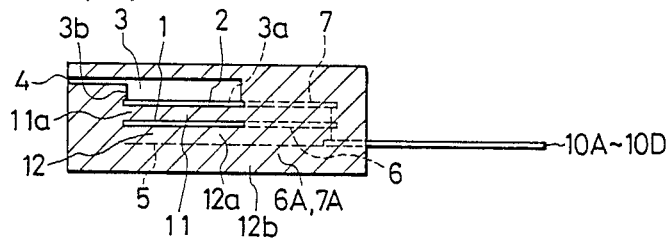

A preferred embodiment of an oxygen sensor is shown in FIGS. 1(A) and 1(B) and is represented generally by the numeral 110. Oxygen sensor 110 may be prepared by printing necessary electrodes 1, 2, a heater 5 and leads 6, 7 on green sheets composed of a solid electrolyte of, for example, zirconia, by screen process printing; pressing and joining the green sheets together into one body; and calcining the combination of them. As embodied herein, and referring to FIGS. 1(A) and 1(B), a detection element 11 is formed on one wall 3a of the walls constituting a space 3. Another wall 3b of space 3 communicates with outside atmosphere via a small diffusion orifice 4 for restricting oxygen diffusion. The negative electrode 2 of the detection element 11 also communicates with the space 3, whereas the positive electrode 1 and negative electrode 2 are formed on respective sides of a layer of zirconia 11A having a suitable thickness of, for example, about 100 $\mu$m.

As herein embodied, a heater element 12 is formed very close to the detection element 11 and has heater 5 embedded between a layer of zirconia 12A having a suitable thickness of, for example, about 100 $\mu$m and a layer of zirconia 12B. Electrodes 1, 2 are connected via the leads 6, 7 to terminals 10A, 10D, whereas heater 5 are connected via leads 6A, 7A to terminals 10B, 10C, respectively.

Preferably, in order to operate the oxygen sensor 110 in the aforesaid configuration, appropriate power is supplied to heater 5 to heat detection element 11 up to a predetermined temperature of, for example, about 450° C. Voltage of, for example, about 1.5 volts is applied across the electrodes 1, 2 with the electrode 1 set at a positive potential and with the electrode 2 at a negative potential. The oxygen content of the outside air can be measured then by measuring the current flowing through the electrode 2. Detection element 11 and heater element 12 are thus layer-built with no air gap therebetween which would add thermal resistance. The necessary operating temperature to be maintained by heater element 12, and the corresponding thermal stresses and fluctuations in characteristics of the oxygen sensor 110 are thus reduced.

Figure 2A:
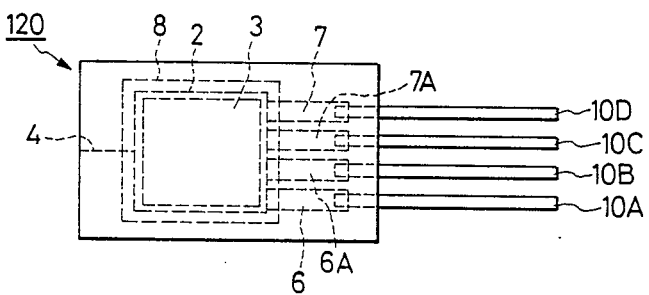
FIGS. 2(A) and 2(B) are schematic top and sectional views, respectively, of a second embodiment of the present invention.
Figure 2B:
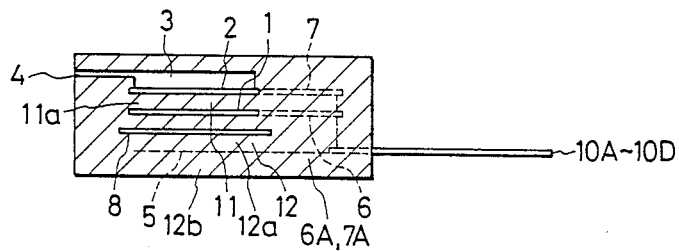

FIGS. 2(A) and 2(B), respectively, are top and sectional views of a second embodiment of the present invention. As herein embodied, oxygen sensor 120 is provided with a shielding electrode 8 installed between electrode 1 of detection element 11 and heater 5 of heater element 12. Consequently, the detection element 11 and the heater element 12 are prevented from electrically interfering with each other when a proper voltage is applied to shielding electrode 8.

Figure 3A:
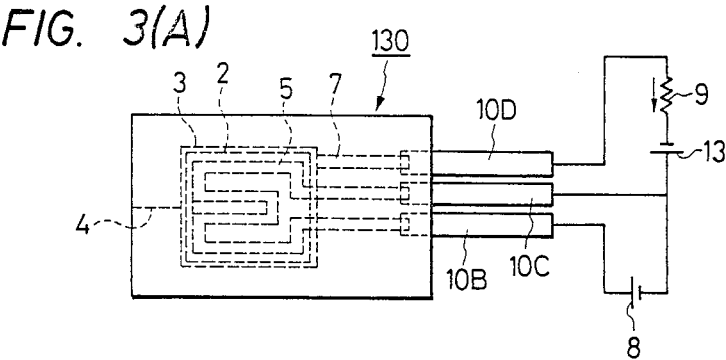
FIGS. 3(A) and 3(B) are schematic top and a sectional view (in principal part), respectively, of a third embodiment of the present invention.
Figure 3B:
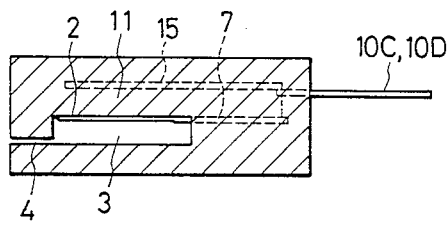

FIGS. 3(A) and 3(B) are top and sectional views of a third embodiment of the present invention, respectively. As herein embodied, oxygen sensor 130 comprises the detection element 11 formed on one side of the space 3 communicating with surrounding outside atmosphere via small diffusion orifice 4 which restricts the diffusion of oxygen. Negative electrode 2 faces space 3. Positive electrode/heater 15 is a positive electrode also used as a heater. Negative electrode 2 is connected via lead 7 to terminal 10D, whereas positive electrode/heater 15 is connected to terminals 10B, 10C. Power supply 8 for positive electrode/heater 15 is connected to the heater terminals 10B, 10C in such a manner that the terminals 10B, 10C are set at positive and negative potential, respectively. Terminal 10D is connected to terminal 10C via a resister 9 for detecting a signal current, and a bias power supply 13.

Figure 5A:
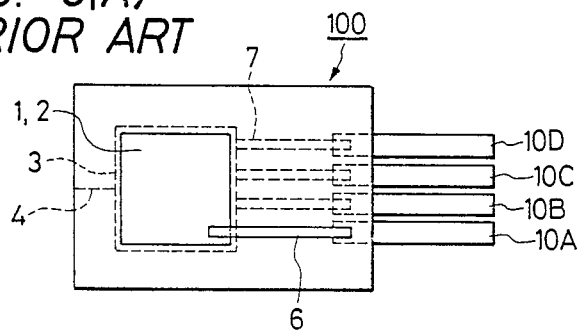
FIGS. 5(A) and 5(B) are schematic top and sectional views, respectively, of a conventional limited current type oxygen sensor.
Figure 5B:
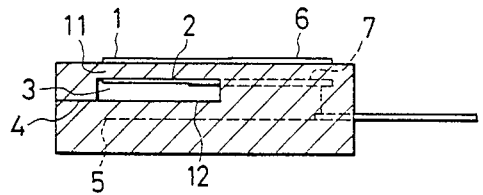
Figure 4:
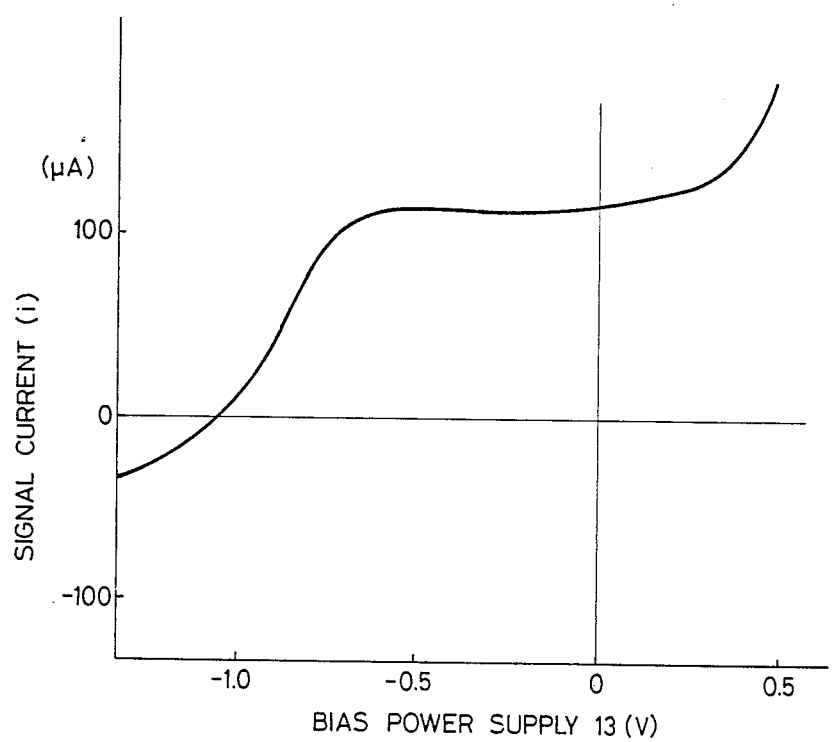
FIG. 4 is a characteristic diagram of the oxygen sensor of FIGS. 3(A) and 3(B).

FIG. 4 shows a characteristic curve of a limited current oxygen sensor of FIGS. 3(A) and 3(B) surrounded by ambient air. The characteristic curve shown in FIG. 4 results from the space 3 having an area of about $2 \times 2$ mm$^2$; the negative electrode having an area of about $2 \times 2$ mm$^2$; positive electrode/heater 15 operating power at about 1.0 W.; and the resistance value of the resister 9 for detecting a signal current at about 100 ohms. Preferably, the electrode 2 is made of platinum, whereas the positive electrode/heater 15 is made of platinum or rhodium. The abscissa and ordinate axes in the characteristic diagram represent the voltage of the bias power supply 13 and the signal current, respectively. Although the zero point of the signal current is shifted to the negative potential side as shown by the curve when the bias voltage is applied across the positive electrode/heater 15 as a positive electrode and the negative electrode 2, this oxygen sensor 130 still shows characteristics similar to conventional oxygen sensor 100 (FIG. 5) and allows the measurement of the oxygen content of the surrounding outside air. In FIG. 4, since the current value at zero bias voltage corresponds to the plateau current value, it is possible to measure the plateau current and thus the oxygen content without using the bias power supply. According to this embodiment, the oxygen content can be measured by means of only the power supply 8 for the positive electrode/heater 15. The requirements for the measurement of oxygen content by means of only the power supply 8 for the positive electrode/heater 15 are met by the following characteristics: the higher the sensor temperature, the closer to the low voltage side the voltage of the power supply 8 for the positive electrode/heater 15 shifts; and the voltage of the power supply 8 therefore shifts to the high voltage side when the sensor 100 temperature is low. The results of the experiments mentioned above revealed that, when the sensor 100 temperature ranges from about 400° to 500° C., about 1 to 3 V. was the fit voltage of the power supply 8 for the positive electrode/heater 15.

In sum and as set forth above, the positive electrode of the detection element is formed of porous material and, together with the heater, embedded in the oxygen ion conductor according to the present invention to effectively conduct the heat produced by the heater to the detection element without the aid of the space. Accordingly, the satisfactory solution of the problems inherent in the prior art are readily furnished in that the reduced thermal resistance across the detection and heater elements lowers the heater temperature and thus prolongs the life of the heater. Further, the reduced temperature difference between the heater element and the remaining portion including the detection element results in reduction of a thermal strain and therefore precludes the possibility of damage to the oxygen sensor and of the occurrence of fluctuations in its characteristics with the effect of having such oxygen sensors readily manufactured.

When the electrical interference of the detection element with the heater element poses a problem, the aforesaid shielding electrode may easily be installed therebetween.

The negative electrode 2 may be connected via the resister 9 for detecting a signal current to the negative potential side of the power supply 8 for the positive electrode/heater 15, so that the oxygen sensor 130 is operated with a smaller amount of power from power supply 8.

It will be apparent to those skilled in the art that various modifications, variations and additions can be made in the present invention without departing from the spirit or scope of the present invention. Thus, it is intended that the present invention cover the modifications and variations provided they come within the general scope of the claims and their equivalents.

What is claimed is:

1. A limited current oxygen sensor, comprising:
    a body having an internal enclosed space therein defined by opposing walls, one of said opposing walls having a diffusion orifice for restricting the amount of oxygen diffused and for connecting the interior space with the exterior of the body; and,
    a solid electrolyte detection means including a heater element and spaced positive and negative electrodes of a predetermined area, said heater and positive electrode being embedded within the walls of the body and not being in communication with said internal space said positive electrode further being porous and being disposed between said negative electrode and said heater element, said negative electrode being disposed in communication with the internal space adjacent another of said opposing walls.

2. A limited current oxygen sensor as recited in claim 1, wherein said body is formed by a plurality of adjacent zirconia layers of approximately 100 $\mu$m in thickness.

3. A limited current oxygen sensor as recited in claim 1, further comprising a shielding electrode installed in said body between said detection element and said heater element.

4. A limited current oxygen sensor as recited in claim 1, further comprising a positive and negative voltage source, and wherein said positive electrode being connected to said positive voltage source, said negative electrode being connected to said negative voltage source.

5. A limited current oxygen sensor as claimed in claim 4, further comprising a resister for detecting a signal current connected in series with said negative electrode and the negative potential side of said power supply.

6. A limited current oxygen sensor as claimed in claim 4, further comprising a resister for detecting a signal current connected between said negative electrode and said power supply.

* * * * *